(12) United States Patent
Xue et al.

(10) Patent No.: US 12,253,509 B2
(45) Date of Patent: Mar. 18, 2025

(54) MULTIPHASE FLOW CYLINDRICAL MODEL TEST SYSTEM AND TEST METHOD

(71) Applicant: INSTITUTE OF ROCK AND SOIL MECHANICS, CHINESE ACADEMY OF SCIENCES, Wuhan (CN)

(72) Inventors: Qiang Xue, Wuhan (CN); Zhixiang Chen, Wuhan (CN); Yong Wan, Wuhan (CN); Mingli Wei, Wuhan (CN); Jiangshan Li, Wuhan (CN); Lei Liu, Wuhan (CN); Yijun Chen, Wuhan (CN); Yuan Li, Wuhan (CN)

(73) Assignee: INSTITUTE OF ROCK AND SOIL MECHANICS, CHINESE ACADEMY OF SCIENCES, Wuhan (CN)

( * ) Notice: Subject to any disclaimer, the term of this patent is extended or adjusted under 35 U.S.C. 154(b) by 273 days.

(21) Appl. No.: 18/048,431

(22) Filed: Oct. 20, 2022

(65) Prior Publication Data

US 2023/0184736 A1    Jun. 15, 2023

(30) Foreign Application Priority Data

Dec. 14, 2021    (CN) .......................... 202111524747.3

(51) Int. Cl.
*G01N 33/24*    (2006.01)
(52) U.S. Cl.
CPC .................................... *G01N 33/24* (2013.01)
(58) Field of Classification Search
CPC ..................................................... G01N 33/24
See application file for complete search history.

(56) References Cited

U.S. PATENT DOCUMENTS

| | | | |
|---|---|---|---|
| 10,809,175 B1 * | 10/2020 | Ayadat | G01N 15/0826 |
| 2022/0136952 A1 * | 5/2022 | Thomas | G01N 33/24 |
| | | | 73/38 |

FOREIGN PATENT DOCUMENTS

| | | | | |
|---|---|---|---|---|
| CN | 202903643 U | * | 4/2013 | |
| CN | 109001098 B | * | 2/2020 | G01N 15/08 |
| CN | 111413263 B | * | 10/2020 | |

(Continued)

*Primary Examiner* — Andre J Allen
(74) *Attorney, Agent, or Firm* — Syncoda LLC; Feng Ma

(57) ABSTRACT

A multiphase flow cylindrical model test system includes a loading structure, a multiphase flow displacement model bucket, a data acquisition and analysis system, a flexible seepage model bucket and a dynamic control system. A multi-parameter test method in the displacement process of pollutants in three-dimensional multi-field and multiphase media is reasonably configured based on the sequential and superimposed application requirements of heat and steam in the thermal enhanced soil vapor extraction process. The disclosure has the following effects: it can conduct array-type measurement of deformation of specimen during the thermal enhanced soil vapor extraction process, measure the temperature field, conductivity field, moisture field, matrix suction distribution, soil pressure distribution, pore water pressure distribution and pollutant discharge rate of the specimen during the test, and realize the flexible wall permeability triaxial test with bidirectional control of the water head and overcome the influence of the polluted liquid on the test equipment.

4 Claims, 5 Drawing Sheets

(56) References Cited

FOREIGN PATENT DOCUMENTS

| | | | | |
|---|---|---|---|---|
| CN | 111650107 B | * | 11/2022 | ............. G01N 13/04 |
| CN | 116124598 A | * | 5/2023 | |
| WO | WO-2018227828 A1 | * | 12/2018 | ............. B01L 3/502 |
| WO | WO-2021042327 A1 | * | 3/2021 | |

\* cited by examiner

MULTIPHASE FLOW CYLINDRICAL MODEL TEST SYSTEM AND TEST METHOD

CROSS-REFERENCE TO RELATED APPLICATION

The present disclosure claims priority to Chinese Patent Application No. 202111524747.3 filed on Dec. 14, 2021, the disclosure of which is hereby incorporated by reference in its entirety.

BACKGROUND

In some implementations, due to the combustion of fossil fuels, the leakage of oil, the agricultural use of industrial sewage and sludge, the stacking of industrial and agricultural solid wastes as well as the widespread use of pesticides, organic pollutants such as phthalates and organochlorine pesticides enter the soil directly or indirectly, and remain in the soil for a long time since the organic pollutants are fat soluble and easily adsorbed by soil particles. Such organic substances contain a variety of carcinogenic, teratogenic or mutagenic substances. If they remain in the soil, they will cause crop yield reduction or even no harvest and will also enter the food chain through plants or animals, which seriously affects human survival and health. Meanwhile, pollutants will change the properties of engineering foundation, cause damage and destruction to works on polluted land foundations and pose health threats to building users. Therefore, carrying out the restoration and treatment of soil organic pollutants has important engineering and social value for ensuring agricultural production, engineering construction and ecological environment safety. In the thermal enhanced soil vapor extraction technology used to solve the above problems, the simulation of the thermal enhanced soil vapor extraction process must have two functions of application and observation of heat and force, and it must be ensured that each test function can operate independently. However, existing thermal enhanced soil vapor extraction devices generally cannot exert a certain vertical force on the soil layer, which affects the simulation effect of pollutant displacement at a certain buried depth. The existing flexible wall triaxial specimen test has the following problems: 1) the polluted liquid brought out during the seepage process cannot be effectively isolated, which will greatly damage the function of the test equipment; 2) the influence of head difference and head pressure on the permeability test at the same time are not taken into consideration, and thus the obtained results cannot be used for reliable analysis of garbage dams under the action of upper and lower water heads; 3) the seepage deformation cannot be quantitatively characterized or the seepage deformation is not considered, and thus the research on the deformation of fluid-solid coupling cannot be satisfied.

That is, for the realization of simulation of multi-field and multiphase process under the stress state of organic polluted soil, especially the analysis of the mechanical problems of large and high landfills, there still exist the following technical problems: the polluted liquid brought out during the seepage process cannot be effectively isolated, the influence of head difference and head pressure on the permeability test at the same time are not taken into consideration, the obtained results cannot be used for reliable analysis of garbage dams under the action of upper and lower water heads, the seepage deformation cannot be quantitatively characterized or the seepage deformation is not considered, and the research on the deformation of fluid-solid coupling cannot be satisfied.

Thus, it is an urgent technical problem to those skilled in the art to propose effective solutions to the realization of simulation of the multi-field and multiphase process under the stress state of organic polluted soil, especially the analysis of the mechanical problems of large and high landfills.

SUMMARY

The disclosure relates to the technical field of geotechnical testing and specifically, to a multiphase flow cylindrical model test system and a test method.

A multiphase flow cylindrical model test system provided by the disclosure aims to at least solve the above technical problems.

To solve the above technical problems, in a first aspect of the disclosure, a multiphase flow cylindrical model test system is provided, comprising: a loading structure, a multiphase flow displacement model bucket, a data acquisition and analysis system, a flexible seepage model bucket and a dynamic control system, wherein: the loading structure is of a gantry type and comprises a T-shaped slide base at the bottom, a connecting shaft at the top, a lead screw and a guide shaft on both sides; a horizontal beam loading mechanism moves up and down with the lead screw and the guide shaft on both sides to apply a load to the multiphase flow displacement model bucket, the lead screw being provided with the guide shaft on its periphery to guide the horizontal beam loading mechanism to move in a fixed direction; an outside of the lead screw and the guide shaft on both sides is wrapped by a profile, upper and lower parts of the horizontal beam loading mechanism being closed by connecting the profile with flexible louvers; a lower surface of the horizontal beam loading mechanism is provided with a force sensor and a displacement sensor so as to observe a loading force and displacement of a specimen in the multiphase flow displacement model bucket; two lifting rings are symmetrically arranged at a lower end of the horizontal beam loading mechanism for the multiphase flow displacement model bucket, a loading cover plate and an air pressure protection plate to be lifted; the T-shaped slide base is of T-shaped, with an upper part being provided with two sliding bars to facilitate the multiphase flow displacement model bucket to slide back and forth on the sliding bars, both ends of the sliding bars being provided with stop pins; the multiphase flow displacement model bucket is a bucket-shaped hollow cavity whose upper and lower parts can be disassembled, with a side wall whose surface is provided with 12 glass windows in four columns and three rows; a thermal enhanced soil vapor extraction pipe is arranged on the axis of a bottom plate of the multiphase flow displacement model, and a total of 12 thermal enhanced soil vapor extraction pipes are scattered in two circles around the axially arranged the thermal enhanced soil vapor extraction pipe at other locations of the bottom plate so as to achieve heating of the specimen and suction of fluid, and a spacing between the thermal enhanced soil vapor extraction pipes in an outer circle and the thermal enhanced soil vapor extraction pipes in an inner circle is equal to a spacing between the thermal enhanced soil vapor extraction pipes in the inner circle and the thermal enhanced soil vapor extraction pipe at the axis; an edge of the bottom plate is connected with the lower part of the multiphase flow displacement model bucket through bolts; the bottom plate is provided with a drainage channel running through an inside and outside of the bottom plate, and an upper part of the bottom plate is provided with a permeable plate so that a liquid formed in the process of thermal enhanced soil vapor extraction is collected through the permeable plate and then discharged through the drainage channel; an air pressure protection plate is arranged at the top of the multiphase flow displacement model bucket, with an edge being connected to the multiphase flow displacement model bucket through bolts; a pressure-charging valve and a pressure relief valve are symmetrically arranged on an upper part of the air pressure protection plate with respect to a center of the air pressure protection plate so as to facilitate filling of an internal pressure of the multiphase flow displacement model bucket and automatic pressure relief when a pressure is too large; a top surface of the specimen inside the multiphase flow displacement model bucket is provided with a loading cover plate; a side wall of the loading cover plate adopts a C-shaped ball sliding mechanism to come into contact with the multiphase flow displacement model bucket so as to ensure that the loading cover plate can slide up and down on an inner wall of the multiphase flow displacement model buckle during the loading process, a lower part of the loading cover plate coming into contact with the specimen through a flexible rubber pad, an arc-shaped sealing sheet being arranged around an upper part of the loading cover plate to realize sealing of a space formed between the loading cover plate, the multiphase flow displacement model bucket and the air pressure protection plate, and the sealed space between the loading cover plate, the multiphase flow displacement model bucket and the air pressure protection plate being pressurized by a dynamic control system through the pressure-charging valve to ensure tight fit of the arc-shaped sealing sheet and an inner wall of the multi-phase flow displacement model bucket so as to ensure sealing effect; a loading rod and a built-in force sensor are arranged at the axis of the upper part of the loading cover plate, an upper end of the loading rod penetrating a linear bearing of the air pressure protection plate to be connected to a force sensor and a displacement sensor of the loading structure, and a lower end of the loading rod being connected to the loading cover plate through the built-in force sensor; the thermal enhanced soil vapor extraction pipes scattered at the bottom of the multiphase flow displacement model bucket have functions of electric heating, temperature testing and gas charging-suctioning, and the turn on and/or turn off of heating and gas control functions of any pipeline can be randomly adjusted, a pressure relief valve being arranged in a middle part of a side wall of the multiphase flow displacement model bucket to facilitate automatic pressure relief when the pressure in the multiphase flow displacement model bucket exceeds a limit; LED ring lightings, cameras and light hoods are arranged outside the 12 glass windows at a surface of the multiphase flow displacement model bucket to provide a stable test light source and take pictures; and a total of 12 circular sensor sockets in four columns and three rows are arranged at a position between the horizontal glass windows of the side wall surface of the multiphase flow displacement model bucket to facilitate insertion of sensors; the data acquisition and analysis system is in communication with the specimen inside the multiphase flow displacement model bucket.

In some embodiments, the data acquisition and analysis system comprises a collector, a combined temperature-conductivity-moisture content sensor, a K-type temperature sensor, a matrix suction sensor, a soil pressure sensor, a pore water pressure sensor and a camera; the combined temperature-conductivity-moisture content sensor, the matrix suction sensor, the soil pressure sensor and the pore water pressure sensor are inserted into the specimen through the circular sensor sockets in a spirally ascending arrangement, and tightened by threads to ensure that a pressure chamber is sealed; the K-type temperature sensor is arranged on a side surface of an inner wall of the thermal enhanced soil vapor extraction pipe to monitor an equilibrium temperature of a contact position of the thermal enhanced soil vapor extraction pipe and the specimen; the bottom plate is connected to the multiphase flow displacement model bucket, and the combined temperature-conductivity-moisture content sensor, the matrix suction sensor, the soil pressure sensor and the pore water pressure sensor are respectively inserted into the specimen through the circular senor sockets in a spirally ascending arrangement; 12 cameras, the LED ring lightings and the light hoods are connected to 12 glass windows at the surface of the multiphase flow displacement model bucket; the specimen is loaded into the multiphase flow displacement model bucket in layers, the loading cover plate being placed on an upper part of the specimen, the loading rod and the built-in force sensor being connected to the loading cover plate, the air pressure protection plate being connected to the upper part of the multiphase flow displacement model bucket, so that the multiphase flow displacement model bucket is formed.

In some embodiments, the flexible seepage model bucket is a cylindrical hollow cavity, with its sidewall surface being uniformly provided with 12 glass windows in four columns and three rows in order to observe deformation of the specimen during the test; a lower part of the flexible seepage model bucket is connected to an edge of a multifunctional base through bolts, and an upper part of the flexible seepage model bucket is connected with a top plate through bolts; an upper part of the multifunctional base of the flexible seepage model bucket is provided with permeable stones, a base seat below the permeable stones being engraved with a spiral line and a through drainage hole, the drainage hole being connected to an external high-hardness PVC water measuring pipe, the high-hardness PVC water measuring pipe being connected to an air pressure valve of the dynamic control system through a buffer chamber; a center of the top plate of the flexible seepage model bucket is formed with a through loading hole to facilitate the loading rod to load the specimen through the loading hole, an upper part of the loading hole being connected with a linear bearing to facilitate the loading rod to move up and down along the linear bearing; one end of the loading rod penetrating the top plate of the flexible seepage model bucket is connected with the built-in force sensor, the other end thereof being connected with the force sensor on a lower surface of the horizontal beam loading mechanism, a lower end of the built-in force sensor being connected with a rigid loading head of an upper cap of the specimen; a water hole is provided inside the upper cap of the specimen to achieve saturation of the specimen and application of a seepage force to the specimen; a lower part of the side wall surface of the flexible seepage model bucket is formed with a confining pressure hole to apply a stable pressure $\sigma_3$ to the specimen through the dynamic control system; an upper part of the side wall surface of the flexible seepage model bucket is formed with a head pipeline hole so that the external dynamic control system is connected with the water hole of the upper cap of the specimen; the high-hardness PVC water measuring pipe is arranged in a vertical direction, and a grating scale coated on an outside of the high-hardness PVC water measuring pipe may read a change of a water level inside the high-hardness PVC water measuring pipe; a semi-permeable membrane is provided at a connection of the buffer chamber and the high-hardness PVC water measuring pipe to prevent a polluted liquid discharged from the specimen from entering the dynamic control system; the specimen wrapped with a rubber film is placed on the permeable stones of the multi-functional base of the flexible seepage model bucket and the rubber film is fastened to the multifunctional base; the permeable stones and the upper cap of the specimen are respectively placed on an upper end of the specimen wrapped with the rubber film and the rubber film is fastened to the upper cap of the specimen; the confining pressure hole and the water hole are respectively connected with the dynamic control system, a cavity of the flexible seepage model bucket being filled with liquid, the camera being connected to a collector of the data acquisition and analysis system, so that the flexible seepage model bucket is formed.

In a second aspect of the disclosure, a test method for a multiphase flow cylindrical model test system is provided, which can be applied for a multiphase flow cylindrical model test system mentioned above. The test method comprises the following steps: assembling a multiphase flow displacement model bucket; pushing the assembled multiphase flow displacement model bucket along two sliding bars of a T-shaped slide base to a position below a loading structure, and connecting an upper end of a loading rod to a force sensor and a displacement sensor of the loading structure; connecting the force sensor, the displacement sensor, a combined temperature-conductivity-moisture content sensor, a K-type temperature sensor, a matrix suction sensor, a soil pressure sensor, a pore water pressure sensor and a camera to a collector of a data acquisition and analysis system; connecting a dynamic control system to a pressure-charging valve of an air pressure protection plate of the multiphase flow displacement model bucket, and connecting an external interface of a thermal enhanced soil vapor extraction pipe of a bottom plate of the multiphase flow displacement model bucket to the dynamic control system, and connecting the loading structure and LED ring lighting to the dynamic control system; by means of the dynamic control system, setting a vertical loading force σv of the loading structure, and setting a pressure P of the pressure-charging valve and a protection value PP of a pressure relief valve, wherein PP is 1.5~1.8 times the pressure P of the pressure-charging valve so as to consolidate the specimen; setting a heating power W of the thermal enhanced soil vapor extraction pipe by the dynamic control system and starting to heat the specimen, and when a reading on the K-type temperature sensor reaches a target temperature T (80° C.≤T≤150° C.), setting a steam delivery pressure Pa of the thermal enhanced soil vapor extraction pipe by the dynamic control system and starting the test; recording a flow state and skeleton deformation of each phase in the specimen during the test by the camera; recording a vertical deformation of the specimen under a stable vertical loading force σv during the test by the force sensor and the displacement sensor; recording a conductivity and a moisture content of test points in the specimen during the test by the combined temperature-conductivity-moisture content sensor; recording a matrix suction of test points in the specimen during the test by the matrix suction sensor; recording a soil pressure and pore water pressure of to-be-tested points by the soil pressure sensor and the pore water pressure sensor, respectively; by means of a return air outlet connected to the dynamic control system, recording a change of a mass m of composition i of pollutants discharged from the return air outlet over time, and stopping the test when a sum of mass Σm of all compositions of pollutants discharged accounts for 80% of a total mass of pollutants in the specimen; according to data and location distribution of to-be-measured points recorded by the combined temperature-conductivity-water content sensor, the matrix suction sensor, the soil pressure sensor and the pore water pressure sensor, drawing a spatial distribution cloud map of a conductivity-water content, matrix suction, soil pressure and pore water pressure by using a spatial difference method; according to a sum of a reading on the built-in force sensor and a pressure P of the pressure-charging valve as a total vertical pressure, drawing a relation curve between the total vertical pressure and the reading of the displacement sensor; drawing a W-Pa-m curve according to a heating power W, a steam delivery pressure Pa and the mass m of composition i of pollutants discharged within a certain time range.

In some embodiments, the test method may further comprise the following steps: step 1) assembling a flexible seepage model bucket; step 2) consolidating the specimen within a certain time by applying a stable pressure $\sigma_3$ to the specimen through the dynamic control system, and observing a deformation of the cylindrical specimen during the test by using the camera; step 3) after a consolidation time reaches, by means of the dynamic control system, applying a water pressure Ph to a water hole of an upper cap of the specimen and applying an air pressure Pd to a buffer chamber connected with the high-hardness PVC water measuring pipe at the same time, recording a change of a water level H in the high-hardness PVC water measuring pipe during time t by using a grating scale coated on outside of the high-hardness PVC water measuring pipe, and calculating a permeability k of polluted soil according to Formula (1):

$$k = \frac{Q \cdot L}{A(P_h - P_d)t},$$

where k is a permeability of polluted soil; Q is an increase amount of water level of the high-hardness PVC water measuring pipe in time t, where $Q=\pi R^2 \cdot \Delta H$, which can be calculated according to an radius R of the high-hardness PVC water measuring pipe and an increase height of water level ΔH, ΔH being the increase height of water level of the high-hardness PVC water measuring pipe in time t; A is a cross-sectional area of the cylindrical specimen with a value of 706.86 cm²; L is a height of the cylindrical specimen with a value of 60 cm; Ph is a water pressure applied to the water hole of the upper cap of the specimen by the dynamic control system, Pd being an air pressure applied to the buffer chamber connected with the high-hardness PVC water measuring pipe by the dynamic control system; t is an recording time; and step 4) keeping a difference between Ph and Pd unchanged and resetting Ph and Pd, recording a change of the water level in the high-hardness PVC water measuring pipe over time under the action of the newly set constant Ph and Pd, and calculating the permeability k of the polluted soil by using Formula (1); step 5) keeping Ph unchanged, resetting Pd and starting the test, recording the change of the water level in the high-hardness PCV water measuring pipe over time under the action of the newly set constant Ph and Pd, and calculating the permeability k of the polluted soil by using Formula (1); step 6) drawing a curve of the permeability k of the polluted soil with Ph and the difference between Ph and Pd according to the permeability k of the polluted soil determined in steps 3), 4) and 5); and step 7)

closing the water pressure Ph applied to the water hole of the upper cap of the specimen and the air pressure Pd applied to the buffer chamber connected to the high-hardness PVC water measuring pipe by the dynamic control system; controlling, by the dynamic control system, a horizontal beam loading mechanism of the loading structure to apply a vertical displacement with a constant rate to the specimen, continuing to record the deformation of the specimen during the test by using the camera, recording, by the displacement sensor, a compression deformation of the specimen, and ending the test when the compression deformation of the specimen recorded by the displacement sensor reaches 15% of a total height of the specimen.

ADVANTAGEOUS EFFECTS

The disclosure has the following effects: the multiphase flow cylindrical model test system can conduct array-type measurement of deformation of specimen during the thermal enhanced soil vapor extraction process, can measure the temperature field, conductivity field, moisture field, matrix suction distribution, soil pressure distribution, pore water pressure distribution and discharge rate of pollutants of the specimen body during the test, and further can realize the flexible wall permeability triaxial test with bidirectional control of the water head and overcome the influence of the polluted liquid on the test equipment. The improvement of the test function can maximize the multiphase and multi-field coupling mechanism in the field of polluted soil and provide a guarantee for the treatment of polluted soil and disaster prevention and mitigation in environmental geotechnical engineering.

BRIEF DESCRIPTION OF THE DRAWINGS

To more clearly illustrate the technical solutions in embodiments of the specification or some implementations, a brief introduction is presented below to the accompanying drawings used in the embodiments. It is apparent that the drawings to be described below are merely some embodiments of the disclosure. For those of ordinary skill in the art, they may further obtain other drawings according to these drawings without the exercise of inventive skill.

Figure 1:
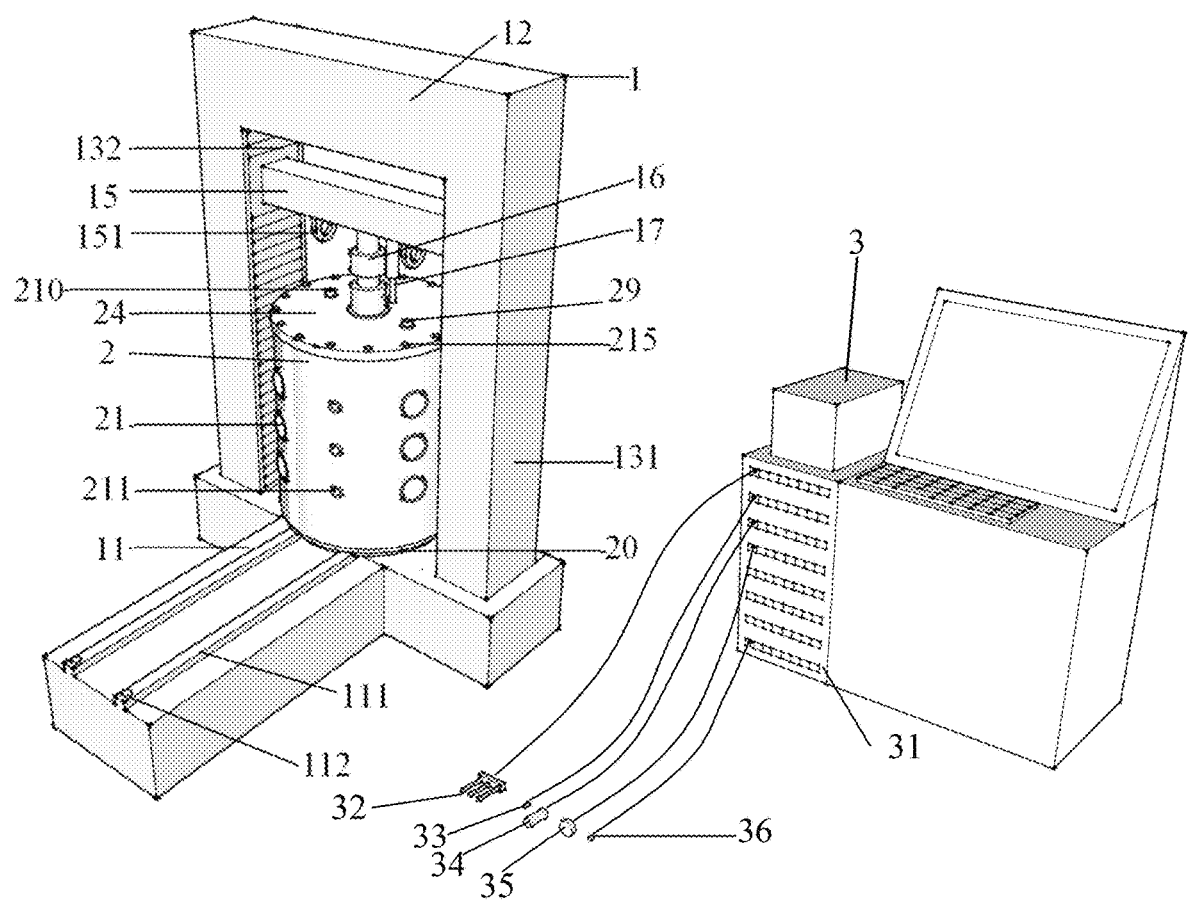
FIG. 1 shows an overall structural diagram of a multiphase flow cylindrical model test system according to some embodiments of the disclosure.

EXPLANATIONS OF REFERENCE NUMERALS 1. loading structure; 2. multiphase flow displacement model bucket; 3. data acquisition and analysis system; 4. flexible seepage model bucket; 5. dynamic control system; 11. T-shaped slide base; 12. connecting shaft at the top; 13. lead screws on both sides; 14. guide shaft 15. horizontal beam loading structure; 16. force sensor; 17. displacement sensor; 20. bottom plate; 21. glass window; 22. thermal enhanced soil vapor extraction pipe; 23. loading cover plate; 24. air pressure protection plate; 25. flexible rubber pad; 26. loading rod; 27. built-in force sensor; 28. linear bearing; 29. pressure relief valve; 31. collector; 32. combined temperature-conductivity-moisture content sensor; 33. K-type temperature sensor; 34. matrix suction sensor; 35. soil pressure sensor; 36. pore water pressure sensor; 37. camera; 41. multifunctional base; 42. top plate; 43. high-hardness PVC water measuring pipe; 44. buffer chamber; 45. upper cap of the specimen; 46. confining pressure hole; 47. head pipeline hole; 111. sliding bar; 112. stop pin; 113. profile; 132. flexible louver; 210. pressure-charging valve; 211. circular sensor socket; 212. LED ring lighting; 213. light hood; 214. arc-shaped sealing sheet; 215. bolt; 216. drainage channel; 217. permeable plate; 231. C-shaped ball sliding mechanism; 411. Permeable stone; 412. spiral line; 413. drainage hole; 414. rubber film; 421. loading hole; 441. semi-permeable membrane; 451. rigid loading head; 452. water hole.

DETAILED DESCRIPTION

The technical solutions in the disclosure will be clearly and completely described in conjunction with the drawings. It is apparently that embodiments to be described are merely a part of the embodiments of the disclosure, rather than all of the embodiments. All other embodiments obtained by those of ordinary skill in the art based on the embodiment of the disclosure fall within the scope of the disclosure.

Meanwhile, in the embodiments of the specification, when a component is "fixed to" a further component, it may be directly on the further component or there may exist an intermediate component. When a component is considered as being "connected to" a further component, it may be directly connected to the further component or there might exist an intermediate component. When a component is considered as being "arranged on" a further component, it may be directly disposed on the further component or there might exist an intermediate component. The terms "vertical," "horizontal," "left," "right" and similar expressions used in the embodiments of the specification are merely for the illustration purpose, rather than limiting the disclosure.

In recent years, the implementation of laws and regulations and rules such as the Soil Pollution Prevention and Control Action Plan as well as the Soil Pollution Prevention and Control Law of the People's Republic of China has provided policy basis and enforcement rules for soil pollution prevention and control. To carry out the treatment and remediation of polluted soil is an inevitable requirement driven by both the soil pollution situation and the policy to face the safety issues of engineering facilities and agricultural production. The treatment or remediation methods of soil organic pollution can be classified into three types: physical method, chemical method and bioremediation method. Thermal enhanced soil vapor extraction technology is a physical method that uses heating and steam transport to pyrolyze and displace pollutants in organic polluted soil. Effectively simulating the multiphase and multi-field coupling process of thermal enhanced soil vapor extraction plays a fundamental role on revealing the mechanism of pollutant migration, rationally determining the parameters of displacement of polluted soil, and assisting the treatment of polluted soil. Based thereon, the disclosure proposes a multiphase flow cylindrical model test system and test method so as to solve corresponding technical problems.

First Embodiment

Figure 2:
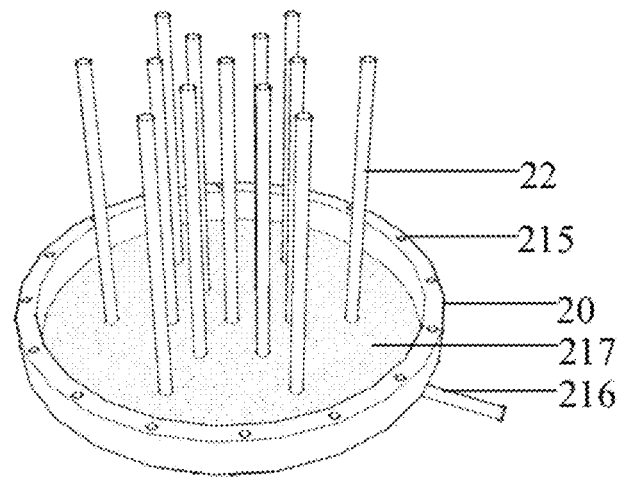
FIG. 2 shows a structural diagram of a bottom plate of a multiphase flow displacement model bucket involved in the disclosure.
Figure 3:
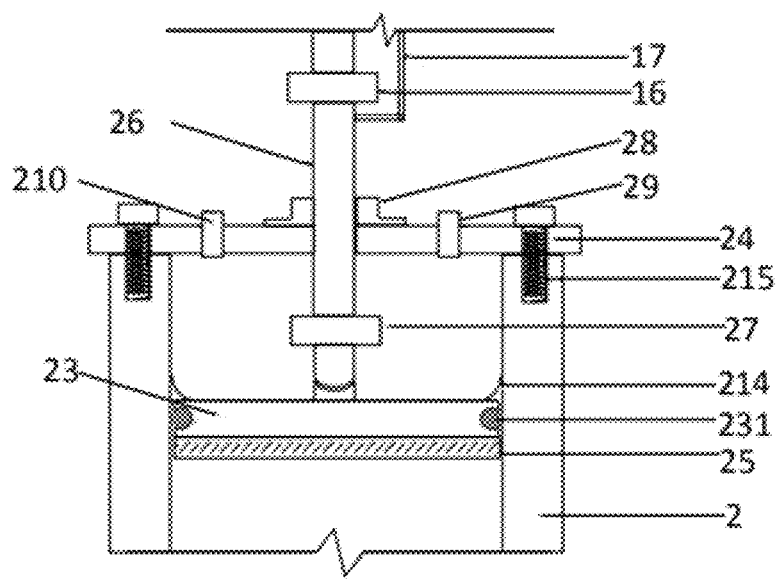
FIG. 3 shows a cross-sectional view of a loading cover plate of a multiphase flow displacement model bucket involved in the disclosure.
Figure 4:
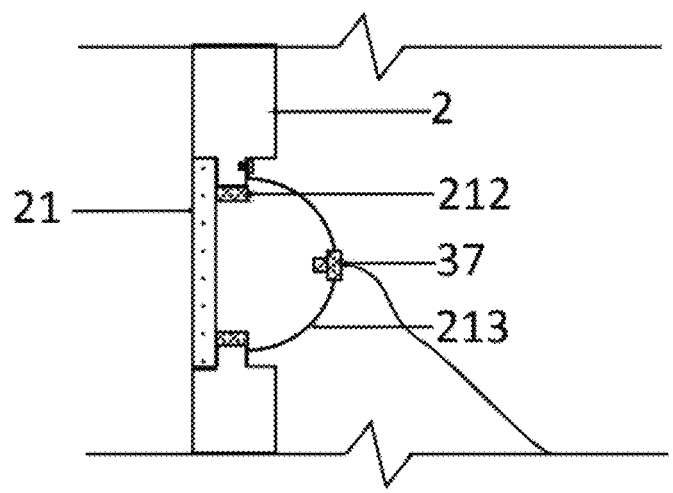
FIG. 4 shows a detailed view of a glass window of a multiphase flow displacement model bucket involved in the disclosure.
Figure 5:
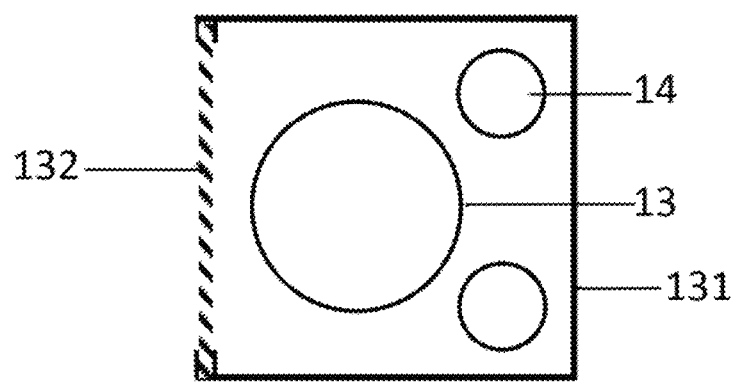
FIG. 5 shows a detailed view of a lead screw and a guide shaft of a loading mechanism involved in the disclosure.
Figure 6:
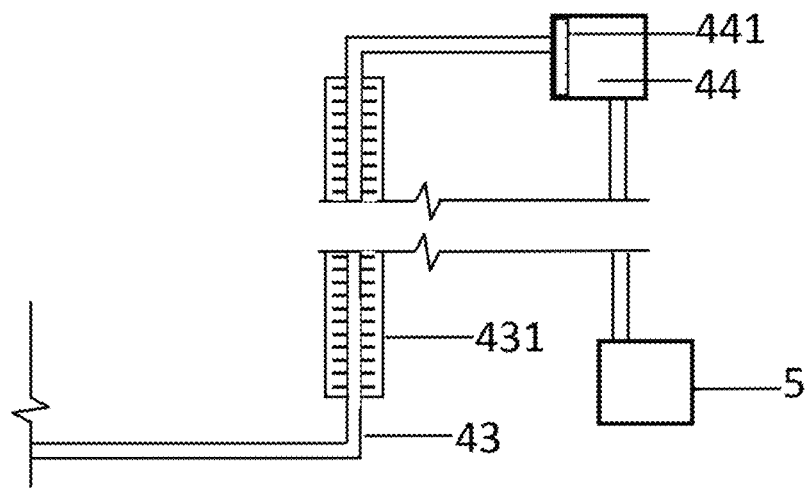
FIG. 6 shows a connection diagram of a high-hardness PVC water measuring pipe involved in the disclosure.
Figure 7:
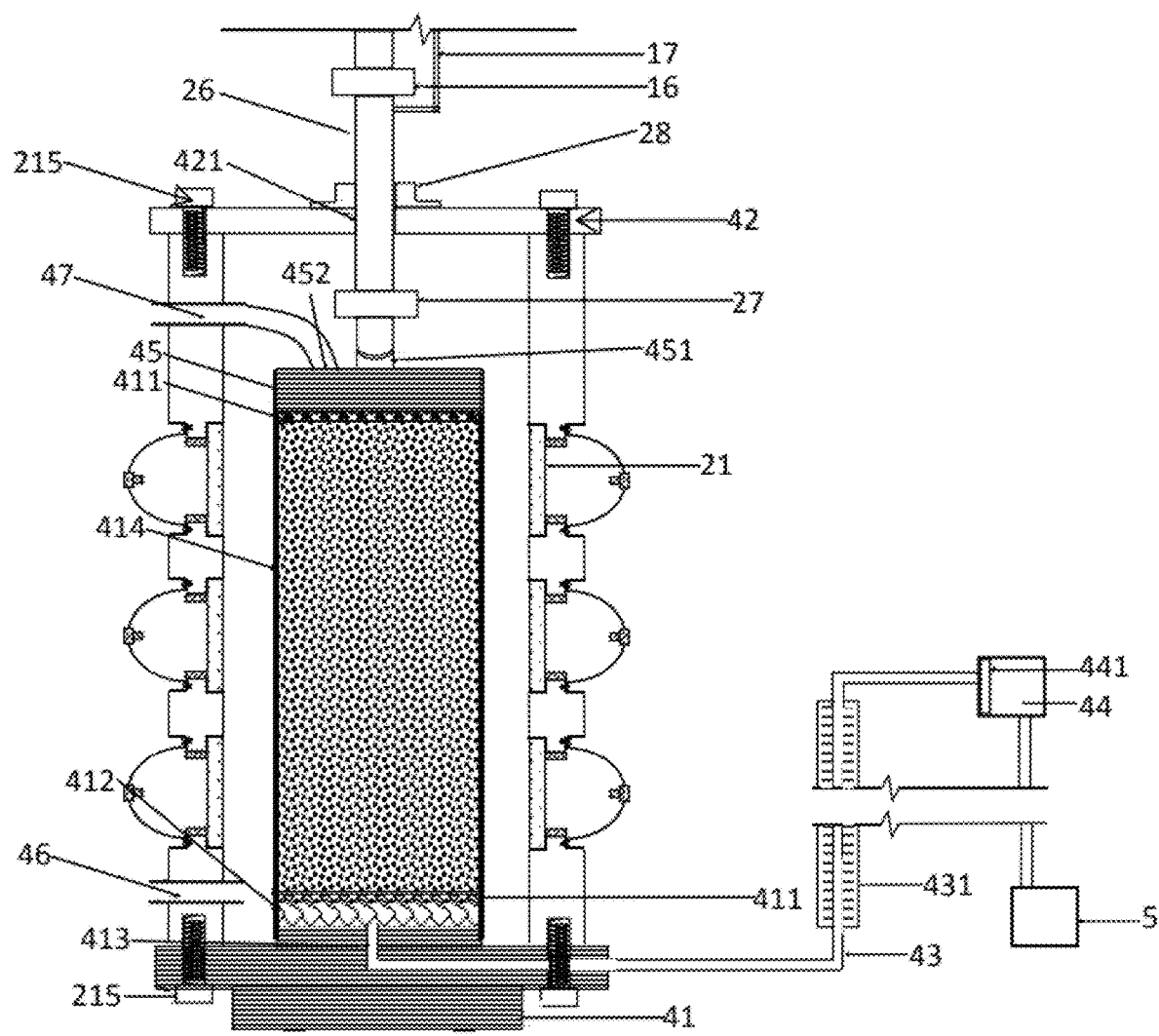
FIG. 7 shows a perspective structural diagram of a flexible seepage model bucket involved in the disclosure.

As shown in FIGS. 1 to 7, this embodiment provides a multiphase flow cylindrical model test system. The test system may include: a loading structure 1, a multiphase flow displacement model bucket 2, a data acquisition and analysis system 3, a flexible seepage model bucket 4 and a dynamic control system 5. The test system is characterized in the following: the loading structure 1 is provided with a gantry type and consists of a T-shaped slide base 11 at the bottom, a connecting shaft 12 at the top, a lead screw 13 and a guide shaft 14 on both sides; a horizontal beam loading mechanism 15 moves up and down with the lead screw 13 and the guide shaft 14 on both sides to apply a load to the multiphase flow displacement model bucket 2, and the lead screw 13 is provided with the guide shaft 14 on its periphery to guide the horizontal beam loading mechanism 15 to move in a fixed direction; the outside of the lead screw 13 and the guide shaft 14 on both sides is wrapped by a profile 131, and the upper and lower parts of the horizontal beam loading mechanism 15 are closed by connecting the profile 131 with flexible louvers 132; the lower surface of the horizontal beam loading mechanism 15 is provided with a force sensor 16 and a displacement sensor 17 so as to observe the loading force and displacement of the specimen in the multiphase flow displacement model bucket 2; two lifting rings 151 are symmetrically arranged at the lower end of the horizontal beam loading mechanism 15 for the multiphase flow displacement model bucket 2, a loading cover plate 23 and an air pressure protection plate 24 to be lifted.

The T-shaped slide base 11 is T-shaped, and two sliding bars 111 are arranged on the upper part to facilitate the multiphase flow displacement model bucket 2 to slide back and forth on the sliding bars so as to facilitate the assembly and disassembly of the specimen, and both ends of the sliding bars 111 are provided with stop pins 112 to prevent the sliding bars 111 from sliding out and causing danger during the moving process of the multiphase flow model bucket 2.

The multiphase flow displacement model bucket 2 is a bucket-shaped hollow cavity whose upper and lower parts can be disassembled, and 12 glass windows 21 in four columns and three rows are provided on the side wall surface so as to observe the flow state and skeleton deformation of each phase in the specimen during the test. A thermal enhanced soil vapor extraction pipe 22 is arranged on the axis of a bottom plate 20 of the multiphase flow displacement model bucket 2. A total of 12 thermal enhanced soil vapor extraction pipes 22 are scattered in two circles around the axially arranged the thermal enhanced soil vapor extraction pipe 22 at other locations of the bottom plate 20 so as achieve heating of the specimen and suction of fluid, and the spacing between the thermal enhanced soil vapor extraction pipes 22 at outer circle and the thermal enhanced soil vapor extraction pipes 22 at inner circle is equal to the spacing between the thermal enhanced soil vapor extraction pipes 22 at inner circle and the thermal enhanced soil vapor extraction pipe 22 at the axial center position. The edge of the bottom plate 20 is connected with the lower part of the multiphase flow displacement model bucket 2 through bolts 215. The bottom plate 20 is provided with a drainage channel 216 running through the inside and outside of the bottom plate, and the upper part of the bottom plate 20 is provided with a permeable plate 217 so that the liquid formed in the process of thermal enhanced soil vapor extraction is collected through the permeable plate 217 and then discharged through the drainage channel 216.

An air pressure protection plate 24 is arranged at the top of the multiphase flow displacement model bucket 2, with the edge being connected to the multiphase flow displacement model bucket 2 through the bolts 215. A pressure-charging valve 210 and a pressure relief valve 29 are symmetrically arranged on the upper part of the air pressure protection plate 24 with respect to the center so as to facilitate the filling of the internal pressure of the multiphase flow displacement model bucket 2 and the automatic pressure relief when the pressure is too large. The top surface of the specimen inside the multiphase flow displacement model bucket 2 is provided with a loading cover plate 23. A side wall of the loading cover plate 23 adopts a C-shaped ball sliding mechanism 231 to come into contact with the multiphase flow displacement model bucket 2 so as to ensure that the loading cover plate 23 can slide up and down on an inner wall of the multiphase flow displacement model bucket 2 during the loading process. The lower part of the loading cover plate 23 comes into contact with the specimen through a flexible rubber pad 25, and an arc-shaped sealing sheet 214 is arranged around the upper part of the loading cover plate 23 to realize the sealing of the space formed between the loading cover plate 23, the multiphase flow displacement model bucket 2 and the air pressure protection plate 24. The sealed space between the loading cover plate 23, the multiphase flow displacement model bucket 2 and the air pressure protection plate 24 is pressurized by a dynamic control system 5 through the pressure-charging valve 210 to ensure the tight fit of the arc-shaped sealing sheet 214 and the inner wall of the multi-phase flow displacement model bucket 2 so as to ensure the sealing effect. A loading rod 26 and a built-in force sensor 27 are arranged at the axis of the upper part of the loading cover plate 23. The upper end of the loading rod 26 penetrates a linear bearing 28 of the air pressure protection plate 24 to be connected to a force sensor 16 and a displacement sensor 17 of the loading structure 1, and the lower end of the loading rod 26 is connected to the loading cover plate 23 through the built-in force sensor 27.

The thermal enhanced soil vapor extraction pipes 22 scattered at the bottom of the multiphase flow displacement model bucket 2 have functions of electric heating, temperature testing and gas charging-suctioning, and the turn on and/or turn off of heating and gas control functions of any pipeline can be randomly adjusted. A pressure relief valve 29 is arranged in the middle part of the side wall of the multiphase flow displacement model bucket 2 to facilitate automatic pressure relief when the pressure in the multiphase flow displacement model bucket 2 exceeds a limit. LED ring lightings 212, cameras 37 and light hoods 213 are arranged outside the 12 glass windows 21 at the surface of the multiphase flow displacement model bucket 2 to provide a stable test light source and take pictures; and a total of 12 circular sensor sockets 211 in four columns and three rows are arranged at the position between the horizontal glass windows 21 of the side wall surface of the multiphase flow displacement model bucket 2 to facilitate the insertion of sensors.

The data acquisition and analysis system 3 consists of a collector 31, a combined temperature-conductivity-moisture content sensor 32, a K-type temperature sensor 33, a matrix suction sensor 34, a soil pressure sensor 35, a pore water pressure sensor 36 and a camera 37. The combined temperature-conductivity-moisture content sensor 32, the matrix suction sensor 34, the soil pressure sensor 35 and the pore water pressure sensor 36 are inserted into the specimen through the circular sensor sockets 211 in a spirally ascending arrangement, and then are tightened by threads to ensure that the pressure chamber is sealed. The K-type temperature sensor 33 is arranged on the side of the inner wall of the thermal enhanced soil vapor extraction pipe 22 to monitor an equilibrium temperature of the contact position of the thermal enhanced soil vapor extraction pipe 22 and the specimen.

The bottom plate 20 is connected to the multiphase flow displacement model bucket 2, and the combined temperature-conductivity-moisture content sensor 32, the matrix suction sensor 34, the soil pressure sensor 35 and the pore water pressure sensor 36 are respectively inserted into the specimen through the circular senor sockets 211 in a spirally ascending arrangement. The 12 cameras 37, LED ring lightings 212 and light hoods 213 are connected to the 12 glass windows at the surface of the multiphase flow displacement model bucket 2. The specimen is loaded into the multiphase flow displacement model bucket 2 in layers. The loading cover plate 23 is placed on the upper part of the specimen. The loading rod 26 and the built-in force sensor 27 are connected to the loading cover plate 23, and the air pressure protection plate 24 is connected to the upper part of the multiphase flow displacement model bucket 2. Thus the multiphase flow displacement model bucket 2 is formed.

The flexible seepage model bucket 4 has the following technical features: the flexible seepage model bucket 4 is a cylindrical hollow cavity, with its sidewall surface being uniformly provided with 12 glass windows 21 in four columns and three rows in order to observe the deformation of the specimen during the test. The lower part of the flexible seepage model bucket 4 is connected to the edge of a multifunctional base 41 through bolts 215, and the upper part thereof is connected with a top plate 42 through bolts 215. The upper part of the multifunctional base 41 of the flexible seepage model bucket 4 is provided with permeable stones 411. A base seat below the permeable stones 411 is engraved with spiral lines 412 and a through drainage hole 413. The drainage hole 413 is connected to an external high-hardness PVC water measuring pipe 43, and the high-hardness PVC water measuring pipe 43 is connected to the air pressure valve of the dynamic control system 5 through a buffer chamber 44.

The center of the top plate 42 of the flexible seepage model bucket 4 is formed with a through loading hole 421 to facilitate the loading rod 26 to load the specimen through the loading hole 421, and the upper part of the loading hole 421 is connected with a linear bearing 28 to facilitate the loading rod 26 to move up and down along the linear bearing 28. One end of the loading rod 26 penetrating the top plate 42 of the flexible seepage model bucket 4 is connected with the built-in force sensor 27, and the other end thereof is connected with the force sensor 16 on the lower surface of the horizontal beam loading mechanism 15. The lower end of the built-in force sensor 27 is connected with a rigid loading head 451 of an upper cap 45 of the specimen.

A water hole 452 is provided inside the upper cap 45 of the specimen to achieve saturation of the specimen and application of a seepage force on the specimen. The lower part of the side wall surface of the flexible seepage model bucket 4 is formed with a confining pressure hole 46 to apply a stable pressure $\sigma_3$ to the specimen through the dynamic control system 5, and the upper part of the side wall surface of the flexible seepage model bucket 4 is formed with a head pipeline hole 47 so that the external dynamic control system 5 can be connected with the water hole 452 of the upper cap 45 of the specimen.

The high-hardness PVC water measuring pipe 43 is arranged in a vertical direction, and a grating scale coated on an outside of the high-hardness PVC water measuring pipe 43 can read the change of the water level inside the high-hardness PVC water measuring pipe 43. A semi-permeable membrane 441 is provided at the connection of the buffer chamber 44 and the high-hardness PVC water measuring pipe 43 to prevent the polluted liquid discharged from the specimen from entering the dynamic control system 5.

The specimen wrapped with a rubber film 414 is placed on the permeable stones 411 of the multifunctional base 41 of the flexible seepage model bucket 4 and the rubber film 414 is fastened to the multifunctional base 41. The permeable stones 411 and the upper cap 45 of the specimen are respectively placed on the upper end of the specimen wrapped with the rubber film 414, and the rubber film 14 is fastened to the upper cap 45 of the specimen. The confining pressure hole 46 and the water hole 452 are respectively connected with the dynamic control system 5. The cavity of the flexible seepage model bucket 4 is filled with liquid, and the camera 37 is connected to the collector 31 of the data acquisition and analysis system 3. Thus, the flexible seepage model bucket 4 is formed.

Second Embodiment

A second embodiment of the disclosure provides a method for implementing a multiphase flow displacement model bucket of a multiphase flow cylindrical model test system. The method includes the following steps:

a multiphase flow displacement model bucket 2 is assembled;

the assembled multiphase flow displacement model bucket 2 is pushed along two sliding bars 111 of a T-shaped slide base 11 to a position below a loading structure 1, and an upper end of a loading rod 26 is connected to a force sensor 16 and a displacement sensor 17 of the loading structure 1;

the force sensor 16, the displacement sensor 17, a combined temperature-conductivity-moisture content sensor 32, a K-type temperature sensor 33, a matrix suction sensor 34, a soil pressure sensor 35, a pore water pressure sensor 36 and a camera 37 are connected to a collector 31 of a data acquisition and analysis system 3;

a dynamic control system 5 is connected to a pressure-charging valve 210 of an air pressure protection plate 24 of the multiphase flow displacement model bucket 2, and an external interface of a thermal enhanced soil vapor extraction pipe 22 of a bottom plate 20 of the multiphase flow displacement model bucket 2 is connected to the dynamic control system 5, and the loading structure 1 and LED ring lighting 212 are connected to the dynamic control system;

by means of the dynamic control system 5, a vertical loading force σv of the loading structure 1 is set, and a pressure P of the pressure-charging valve 210 is set, and a protection value PP of a pressure relief valve is set to 1.5~1.8 times the pressure P of the pressure-charging valve 210 so as to consolidate the specimen;

a heating power W of the thermal enhanced soil vapor extraction pipe 22 is set through the dynamic control system 5 and the specimen starts to be heated, and when a reading on the K-type temperature sensor 33 reaches a target temperature T: 80° C.≤T≤150° C., a steam delivery pressure Pa of the thermal enhanced soil vapor extraction pipe 22 is set through the dynamic control system 5 and the test starts;

the flow state and skeleton deformation of each phase in the specimen during the test are recorded by the camera 37; the vertical deformation of the specimen under the stable vertical loading force σv during the test is recorded by the force sensor 16 and the displacement sensor 17; the conductivity and the moisture content of test points in the specimen during the test are recorded by the combined temperature-conductivity-moisture content sensor 32; the matrix suction of test points in the specimen during the test is recorded by the matrix suction sensor 34; the soil pressure and pore water pressure of to-be-tested points are recorded by the soil pressure sensor 35 and the pore water pressure sensor 36, respectively;

through a return air outlet connected to the dynamic control system 5, the change of a mass m of composition i of pollutants discharged from the return air outlet is recorded over time, and the test stops when a sum of mass Σm of all compositions of pollutants discharged accounts for 80% of the total mass of pollutants in the specimen;

according to data and location distribution of to-be-measured points recorded by the combined temperature-conductivity-water content sensor 32, the matrix suction sensor 34, the soil pressure sensor 35 and the pore water pressure sensor 36, a spatial distribution cloud map of the conductivity-water content, matrix suction, soil pressure and pore water pressure is drawn using a spatial difference method; and according to a sum of the reading on the built-in force sensor 27 and the pressure P of the pressure-charging valve 210 as the total vertical pressure, a relation curve between the total vertical pressure and the reading of the displacement sensor 17 is drawn; a W-Pa-m curve is drawn according to the heating power W, the steam delivery pressure Pa and the mass m of composition i of the pollutants discharged within a certain time range.

Further, the method includes the following steps:

step 1): a flexible seepage model bucket 4 is assembled;

step 2): the specimen is consolidated within a certain time by applying a stable pressure $\sigma_3$ to the specimen through the dynamic control system 5, and the deformation of the cylindrical specimen during the test is observed using the camera 37;

step 3): after the consolidation time reaches, by means of the dynamic control system 5, the water pressure Ph is applied to the water hole 452 of the upper cap 45 of the specimen and the air pressure Pd is applied to the buffer chamber 44 connected with the high-hardness PVC water measuring pipe 43 at the same time, and the change of the water level H in the high-hardness PVC water measuring pipe 43 during time t is recorded using a grating scale coated on the outside of the high-hardness PVC water measuring pipe 43, and the permeability k of polluted soil is calculated according to Formula (1), which is:

$$k = \frac{Q \cdot L}{A(P_h - P_d)t} \quad (1)$$

in Formula (1), k is the permeability of polluted soil; Q is an increase amount of water level of the high-hardness PVC water measuring pipe in time t, where Q=πR2·ΔH, which can be calculated according to the radius R of the high-hardness PVC water measuring pipe 43 and an increase height of water level ΔH, ΔH being the increase height of water level of the high-hardness PVC water measuring pipe 43 in time t; A is a cross-sectional area of the cylindrical specimen with a value of 706.86 cm$^2$; L is a height of the cylindrical specimen with a value of 60 cm; Ph is a water pressure applied to the water hole 452 of the upper cap 45 of the specimen by the dynamic control system 5, and Pd is an air pressure applied to the buffer chamber 44 connected with the high-hardness PVC water measuring pipe 43 by the dynamic control system 5; t is a recording time;

step 4): the difference between Ph and Pd is kept unchanged, and Ph and Pd are reset, and the change of the water level in the high-hardness PVC water measuring pipe 43 over time under the action of the newly set Ph and Pd is recorded, and the permeability k of the polluted soil is calculated using Formula (1);

step 5): Ph is kept unchanged, Pd is reset and the test starts, and at the same time the change of the water level in the high-hardness PCV water measuring pipe 43 over time under the action of the newly set Ph and Pd is recorded, and the permeability k of the polluted soil is calculated using Formula (1);

step 6): the curve of the permeability k of polluted soil with Ph and the difference between Ph and Pd is drawn according to the permeability k of the polluted soil determined in steps 3), 4) and 5); and step 7): the water pressure Ph applied to the water hole 452 of the upper cap 45 of the specimen and the air pressure Pd applied to the buffer chamber 44 connected to the high-hardness PVC water measuring pipe 43 are respectively closed by the dynamic control system 5; then the horizontal beam loading mechanism 15 of the loading structure 1 is controlled by the dynamic control system 5 to apply a vertical displacement with a constant rate to the specimen, and the camera 37 continues to record the deformation of the specimen during the test, the displacement sensor 17 records the compression deformation of the specimen, and the test ends when the compression deformation of the specimen recorded by the displacement sensor 17 reaches 15% of the total height of the specimen.

The disclosure has the following characteristics:

the spirally ascending arrangement can obtain the multi-parameter distribution field test requirements to a maximum extent;

the sealing performance under large-area loading can be improved based on the dual-chamber air pressure seal;

by using the water head and air pressure to apply the water head difference to the two ends respectively, the permeability performance of the polluted soil dam and the barrier structure under the hydraulic action of the two ends can be simulated, and the impact of the polluted soil leachate on the downstream test sensors can be isolated;

with thinner tubes than diaphragm pumps and water pressure generator cylinders, the test precision of the permeability performance can be increased; and the array-based image measurement method can improve the recording and microscopic analysis of multi-field and multiphase seepage test process.

Since the second embodiment and the first embodiment belong to embodiments under the same inventive concept and some of their structures are completely the same, the structure in the second embodiment that is substantially the same as that in the first embodiment is not described in detail, for which reference may be made to the first embodiment.

Finally, it is noteworthy that the above embodiments are merely specific implementations of the disclosure and are intended to illustrate the technical solutions of the disclosure rather than limiting. The protection scope of the disclosure is not limited to this. Although the disclosure has been illustrated in detail with reference to the foregoing embodiments, those of ordinary skill in the art should understand that: any skilled in the art can still make modifications or easily conceive of changes to the technical solutions described in the foregoing embodiments or make equivalent replacements to some of the technical features within the technical scope disclosed by the disclosure; these modifications, changes or replacements do not make the essence of the corresponding technical solutions depart from the scope of the technical solutions of the embodiments of the disclosure and should be covered within the protection scope of the disclosure. Therefore, the protection scope of the disclosure should be as defined by the claims.

Although the implementation solution of the disclosure has been disclosed above, the disclosure is not limited to the application listed in the specification and the implementations, and it can be applied to various fields suitable for the disclosure. Additional modifications would readily be implemented by those skilled in the art. Therefore, the disclosure is not limited to specific details and illustrations shown and described herein, without departing from the general concept defined by the claims and the equivalent scope.

What is claimed is:

1. A multiphase flow cylindrical model test system, comprising: a loading structure (1), a multiphase flow displacement model bucket (2), a data acquisition and analysis system (3), a flexible seepage model bucket (4) and a dynamic control system (5), wherein:

the loading structure (1) is of a gantry type and comprises a T-shaped slide base (11) at the bottom, a connecting shaft (12) at the top, a lead screw (13) and a guide shaft (14) on both sides, a horizontal beam loading mechanism (15) moving up and down with the lead screw (13) and the guide shaft (14) on both sides to apply a load to the multiphase flow displacement model bucket (2), the lead screw (13) being provided with the guide shaft (14) on its periphery to guide the horizontal beam loading mechanism (15) to move in a fixed direction; an outside of the lead screw (13) and the guide shaft (14) on both sides is wrapped by a profile (131), upper and lower parts of the horizontal beam loading mechanism (15) being closed by connecting the profile (131) with flexible louvers (132); a lower surface of the horizontal beam loading mechanism (15) is provided with a force sensor (16) and a displacement sensor (17) so as to observe a loading force and displacement of a specimen in the multiphase flow displacement model bucket (2); two lifting rings (151) are symmetrically arranged at a lower end of the horizontal beam loading mechanism (15) for the multiphase flow displacement model bucket (2), a loading cover plate (23) and an air pressure protection plate (24) to be lifted;

the T-shaped slide base (11) is of T-shaped, with an upper part being provided with two sliding bars (111) to facilitate the multiphase flow displacement model bucket (2) to slide back and forth on the sliding bars, both ends of the sliding bars (111) being provided with stop pins (112);

the multiphase flow displacement model bucket (2) is a bucket-shaped hollow cavity whose upper and lower parts are able to be disassembled, with a side wall whose surface is provided with 12 glass windows (21) in four columns and three rows; a thermal enhanced soil vapor extraction pipe (22) is arranged on the axis of a bottom plate (20) of the multiphase flow displacement model (2), and a total of 12 thermal enhanced soil vapor extraction pipes (22) are scattered in two circles around the axially arranged the thermal enhanced soil vapor extraction pipe (22) at other locations of the bottom plate (20) so as to achieve heating of the specimen and suction of fluid, and a spacing between the thermal enhanced soil vapor extraction pipes (22) in an outer circle and the thermal enhanced soil vapor extraction pipes (22) in an inner circle is equal to a spacing between the thermal enhanced soil vapor extraction pipes (22) in the inner circle and the thermal enhanced soil vapor extraction pipe (22) at the axis; an edge of the bottom plate (20) is connected with the lower part of the multiphase flow displacement model bucket (2) through bolts (215); the bottom plate (20) is provided with a drainage channel (216) running through an inside and outside of the bottom plate (20), and an upper part of the bottom plate (20) is provided with a permeable plate (217) so that a liquid formed in the process of thermal enhanced soil vapor extraction is collected through the permeable plate (217) and then discharged through the drainage channel (216);

an air pressure protection plate (24) is arranged at the top of the multiphase flow displacement model bucket (2), with an edge being connected to the multiphase flow displacement model bucket (2) through bolts (215); a pressure-charging valve (210) and a pressure relief valve (29) are symmetrically arranged on an upper part of the air pressure protection plate (24) with respect to a center of the air pressure protection plate (24) so as to facilitate filling of an internal pressure of the multiphase flow displacement model bucket (2) and automatic pressure relief when a pressure is too large; a top surface of the specimen inside the multiphase flow displacement model bucket (2) is provided with a loading cover plate (23); a side wall of the loading cover plate (23) adopts a C-shaped ball sliding mechanism (231) to come into contact with the multiphase flow displacement model bucket (2) so as to ensure that the loading cover plate (23) is able to slide up and down on an inner wall of the multiphase flow displacement model bucket (2) u during the loading process, a lower part of the loading cover plate (23) coming into contact with the specimen through a flexible rubber pad (25), an arc-shaped sealing sheet (214) being arranged around an upper part of the loading cover plate (23) to realize sealing of a space formed between the loading cover plate (23), the multiphase flow displacement model bucket (2) and the air pressure protection plate (24), and the sealed space between the loading cover plate (23), the multiphase flow displacement model bucket (2) and the air pressure protection plate (24) being pressurized by a dynamic control system (5) through the pressure-charging valve (210) to ensure tight fit of the arc-shaped sealing sheet (214) and an inner wall of the multi-phase flow displacement model bucket (2) so as to ensure sealing effect; a loading rod

(26) and a built-in force sensor (27) are arranged at the axis of the upper part of the loading cover plate (23), an upper end of the loading rod (26) penetrating a linear bearing (28) of the air pressure protection plate (24) to be connected to a force sensor (16) and a displacement sensor (17) of the loading structure (1), and a lower end of the loading rod (26) being connected to the loading cover plate (23) through the built-in force sensor (27);

the thermal enhanced soil vapor extraction pipes (22) are scattered at the bottom of the multiphase flow displacement model bucket (2), a pressure relief valve (29) being arranged in a middle part of a side wall of the multiphase flow displacement model bucket (2) to facilitate automatic pressure relief when the pressure in the multiphase flow displacement model bucket (2) exceeds a limit; LED ring lightings (212), cameras (37) and light hoods (213) are arranged outside the 12 glass windows (21) at a surface of the multiphase flow displacement model bucket (2) to provide a stable test light source and take pictures; and a total of 12 circular sensor sockets (211) in four columns and three rows are arranged at a position between the horizontal glass windows (21) of the side wall surface of the multiphase flow displacement model bucket (2) to facilitate insertion of sensors;

the data acquisition and analysis system (3) is in communication with the specimen inside the multiphase flow displacement model bucket (2);

the flexible seepage model bucket (4) is a cylindrical hollow cavity, with its sidewall surface being uniformly provided with 12 glass windows (21) in four columns and three rows in order to observe deformation of the specimen during the test; a lower part of the flexible seepage model bucket (4) is connected to an edge of a multifunctional base (41) through bolts (215), and an upper part of the flexible seepage model bucket (4) is connected with a top plate (42) through bolts (215); an upper part of the multifunctional base (41) of the flexible seepage model bucket (4) is provided with permeable stones (411), a base seat below the permeable stones (411) being engraved with a spiral line (412) and a through drainage hole (413), the drainage hole (413) being connected to an external high-hardness PVC water measuring pipe (43), the high-hardness PVC water measuring pipe (43) being connected to an air pressure valve of the dynamic control system (5) through a buffer chamber (44);

a center of the top plate (42) of the flexible seepage model bucket (4) is formed with a through loading hole (421) to facilitate the loading rod (26) to load the specimen through the loading hole (421), an upper part of the loading hole (421) being connected with a linear bearing (28) to facilitate the loading rod (26) to move up and down along the linear bearing (28); one end of the loading rod (26) penetrating the top plate (42) of the flexible seepage model bucket (4) is connected with the built-in force sensor (27), the other end thereof being connected with the force sensor (16) on a lower surface of the horizontal beam loading mechanism (15), a lower end of the built-in force sensor (27) being connected with a rigid loading head (451) of an upper cap (45) of the specimen;

a water hole (452) is provided inside the upper cap (45) of the specimen to achieve saturation of the specimen and application of a seepage force to the specimen; a lower part of the side wall surface of the flexible seepage model bucket (4) is formed with a confining pressure hole (46) to apply a stable pressure $\sigma_3$ to the specimen through the dynamic control system (5); an upper part of the side wall surface of the flexible seepage model bucket (4) is formed with a head pipeline hole (47) so that the external dynamic control system (5) is connected with the water hole (452) of the upper cap (45) of the specimen;

the high-hardness PVC water measuring pipe (43) is arranged in a vertical direction, and a grating scale coated on an outside of the high-hardness PVC water measuring pipe (43) may read a change of a water level inside the high-hardness PVC water measuring pipe (43); a semi-permeable membrane (441) is provided at a connection of the buffer chamber (44) and the high-hardness PVC water measuring pipe (43) to prevent a polluted liquid discharged from the specimen from entering the dynamic control system (5); and the specimen wrapped with a rubber film (414) is placed on the permeable stones (411) of the multifunctional base (41) of the flexible seepage model bucket (4) and the rubber film (414) is fastened to the multifunctional base (41); the permeable stones (411) and the upper cap (45) of the specimen are respectively placed on an upper end of the specimen wrapped with the rubber film (414) and the rubber film (414) is fastened to the upper cap (45) of the specimen; the confining pressure hole (46) and the water hole (452) are respectively connected with the dynamic control system (5), a cavity of the flexible seepage model bucket (4) being filled with liquid, the camera (37) being connected to a collector (31) of the data acquisition and analysis system (3), so that the flexible seepage model bucket (4) is formed.

2. The multiphase flow cylindrical model test system of claim 1, wherein the data acquisition and analysis system (3) comprises a collector (31), a combined temperature-conductivity-moisture content sensor (32), a K-type temperature sensor (33), a matrix suction sensor (34), a soil pressure sensor (35), a pore water pressure sensor (36) and a camera (37); the combined temperature-conductivity-moisture content sensor (32), the matrix suction sensor (34), the soil pressure sensor (35) and the pore water pressure sensor (36) are inserted into the specimen through the circular sensor sockets (211) in a spirally ascending arrangement, and tightened by threads to ensure that a pressure chamber is sealed; the K-type temperature sensor (33) is arranged on a side surface of an inner wall of the thermal enhanced soil vapor extraction pipe (22) to monitor an equilibrium temperature of a contact position of the thermal enhanced soil vapor extraction pipe (22) and the specimen; and the bottom plate (20) is connected to the multiphase flow displacement model bucket (2), and the combined temperature-conductivity-moisture content sensor (32), the matrix suction sensor (34), the soil pressure sensor (35) and the pore water pressure sensor (36) are respectively inserted into the specimen through the circular senor sockets (211) in a spirally ascending arrangement; 12 cameras (37), the LED ring lightings (212) and the light hoods (213) are connected to the 12 glass windows at the surface of the multiphase flow displacement model bucket (2); the specimen is loaded into the multiphase flow displacement model bucket (2) in layers, the loading cover plate (23) being placed on an upper part of the specimen, the loading rod (26) and the built-in force sensor (27) being connected to the loading cover plate (23), the air pressure protection plate (24) being connected to the upper part of the multiphase flow displacement model bucket (2), so that the multiphase flow displacement model bucket (2) is formed.

3. A test method for a multiphase flow cylindrical model test system, applied to the multiphase flow cylindrical model test system according to claim 1, wherein the test method comprises the following steps:
assembling a multiphase flow displacement model bucket (2);
pushing the assembled multiphase flow displacement model bucket (2) along two sliding bars (111) of a T-shaped slide base (11) to a position below a loading structure (1), and connecting an upper end of a loading rod (26) to a force sensor (16) and a displacement sensor (17) of the loading structure (1);
connecting the force sensor (16), the displacement sensor (17), a combined temperature-conductivity-moisture content sensor (32), a K-type temperature sensor (33), a matrix suction sensor (34), a soil pressure sensor (35), a pore water pressure sensor (36) and a camera (37) to a collector (31) of a data acquisition and analysis system (3);
connecting a dynamic control system (5) to a pressure-charging valve (210) of an air pressure protection plate (24) of the multiphase flow displacement model bucket (2), and connecting an external interface of a thermal enhanced soil vapor extraction pipe (22) of a bottom plate (20) of the multiphase flow displacement model bucket (2) to the dynamic control system (5), and connecting the loading structure (1) and LED ring lighting (212) to the dynamic control system;
by the dynamic control system (5), setting a vertical loading force σv of the loading structure (1), and setting a pressure P of the pressure-charging valve (210) and a protection value PP of a pressure relief valve, wherein PP is 1.5~1.8 times the pressure P of the pressure-charging valve (210) so as to consolidate the specimen;
setting a heating power W of the thermal enhanced soil vapor extraction pipe (22) by the dynamic control system (5) and starting to heat the specimen, and when a reading on the K-type temperature sensor (33) reaches a target temperature T, 80° C.≤T≤150° C., setting a steam delivery pressure Pa of the thermal enhanced soil vapor extraction pipe (22) by the dynamic control system (5) and starting the test;
recording a flow state and skeleton deformation of each phase in the specimen during the test by the camera (37); recording a vertical deformation of the specimen under a stable vertical loading force σv during the test by the force sensor (16) and the displacement sensor (17); recording a conductivity and a moisture content of test points in the specimen during the test by the combined temperature-conductivity-moisture content sensor (32); recording a matrix suction of test points in the specimen during the test by the matrix suction sensor (34); recording a soil pressure and pore water pressure of to-be-tested points by the soil pressure sensor (35) and the pore water pressure sensor (36), respectively;
by a return air outlet connected to the dynamic control system (5), recording a change of a mass m of composition i of pollutants discharged from the return air outlet over time, and stopping the test when a sum of mass Σm of all compositions of pollutants discharged accounts for 80% of a total mass of pollutants in the specimen;
according to data and location distribution of to-be-measured points recorded by the combined temperature-conductivity-water content sensor (32), the matrix suction sensor (34), the soil pressure sensor (35) and the pore water pressure sensor (36), drawing a spatial distribution cloud map of a conductivity-water content, matrix suction, soil pressure and pore water pressure by using a spatial difference method; and
according to a sum of a reading on the built-in force sensor (27) and a pressure P of the pressure-charging valve (210) as a total vertical pressure, drawing a relation curve between the total vertical pressure and the reading of the displacement sensor (17); drawing a W-Pa-m curve according to a heating power W, a steam delivery pressure Pa and the mass m of composition i of pollutants discharged within a certain time range.

4. The test method according to claim 3, further comprising:
step 1): assembling a flexible seepage model bucket (4);
step 2): consolidating the specimen within a certain time by applying a stable pressure $\sigma_3$ to the specimen through the dynamic control system (5), and observing a deformation of the cylindrical specimen during the test by using the camera (37);
step 3) after a consolidation time reaches, by the dynamic control system (5), applying a water pressure Ph to a water hole (452) of an upper cap (45) of the specimen and applying an air pressure Pd to a buffer chamber (44) connected with the high-hardness PVC water measuring pipe (43) at the same time, recording a change of a water level H in the high-hardness PVC water measuring pipe (43) during time t by using a grating scale coated on outside of the high-hardness PVC water measuring pipe (43), and calculating a permeability k of polluted soil according to Formula (1):

$$k = \frac{Q \cdot L}{A(P_h - P_d)t} \quad (1)$$

where k is a permeability of polluted soil; Q is an increase amount of water level of the high-hardness PVC water measuring pipe (43) in time t, where $Q=\pi R^2 \cdot \Delta H$, which is able to be calculated according to an radius R of the high-hardness PVC water measuring pipe (43) and an increase height of water level ΔH, ΔH being the increase height of water level of the high-hardness PVC water measuring pipe (43) in time t; A is a cross-sectional area of the cylindrical specimen with a value of 706.86 cm$^2$; L is a height of the cylindrical specimen with a value of 60 cm; Ph is a water pressure applied to the water hole (452) of the upper cap (45) of the specimen by the dynamic control system (5), Pd being an air pressure applied to the buffer chamber (44) connected with the high-hardness PVC water measuring pipe (43) by the dynamic control system (5); t is an recording time;
step 4): keeping a difference between Ph and Pd unchanged and resetting Ph and Pd, recording a change of the water level in the high-hardness PVC water measuring pipe (43) over time under the action of the newly set Ph and Pd, and calculating the permeability k of the polluted soil by using Formula (1);
step 5): keeping Ph unchanged, resetting Pd and starting the test, recording the change of the water level in the high-hardness PCV water measuring pipe (43) over time under the action of the newly set Ph and Pd, and calculating the permeability k of the polluted soil by using Formula (1);

step 6): drawing a curve of the permeability k of the polluted soil with Ph and the difference between Ph and Pd according to the permeability k of the polluted soil determined in steps 3), 4) and 5); and step 7): closing the water pressure Ph applied to the water hole (452) of the upper cap (45) of the specimen and the air pressure Pd applied to the buffer chamber (44) connected to the high-hardness PVC water measuring pipe (43) by the dynamic control system (5); controlling, by the dynamic control system (5), a horizontal beam loading mechanism (15) of the loading structure (1) to apply a vertical displacement with a constant rate to the specimen, continuing to record the deformation of the specimen during the test by using the camera (37), recording, by the displacement sensor (17), a compression deformation of the specimen, and ending the test when the compression deformation of the specimen recorded by the displacement sensor (17) reaches 15% of a total height of the specimen.

\* \* \* \* \*